United States Patent [19]

Kaplan et al.

[11] 4,322,362

[45] Mar. 30, 1982

[54] SALTS OF 2-HYDROXYMALONATE PLATINUM COMPLEXES

[75] Inventors: Murray A. Kaplan, Syracuse, N.Y.; Alphonse P. Granatek, Scotsdale, Ariz.

[73] Assignee: Bristol-Myers Company, New York, N.Y.

[21] Appl. No.: 227,324

[22] Filed: Jan. 22, 1981

Related U.S. Application Data

[63] Continuation-in-part of Ser. No. 172,805, Jul. 28, 1980, abandoned, which is a continuation-in-part of Ser. No. 153,117, May 27, 1980, abandoned.

[51] Int. Cl.$^3$ ............................................. C07F 15/00
[52] U.S. Cl. ................................................ 260/429 R
[58] Field of Search ..................................... 260/429 R

[56] References Cited

U.S. PATENT DOCUMENTS 4,115,418  9/1978  Gale et al. ...................... 260/429 R
4,140,707  2/1979  Cleare et al. ................... 260/429 R

*Primary Examiner*—Helen M. S. Sneed
*Attorney, Agent, or Firm*—David M. Morse

[57] ABSTRACT

Disclosed are water-soluble salts of the known coordination compounds 2-hydroxymalonato diammine platinum (II), 2-hydroxymalonato (1,2-diaminocyclohexane)platinum (II) and 2-hydroxymalonato (1,1-diaminomethylcyclohexane)platinum (II). The novel sodium and ammonium salts of the present invention possess high water-solubility, thus allowing intravenous dosage forms to be prepared.

30 Claims, 4 Drawing Figures

INFRARED ABSORPTION SPECTRUM
OF 2-HYDROXYMALONATO (1,1-DIAMINOMETHYLCYCLOHEXANE)
PLATINUM (II), SODIUM SALT

SALTS OF 2-HYDROXYMALONATE PLATINUM COMPLEXES

CROSS-REFERENCE TO RELATED APPLICATIONS

This application is a continuation-in-part of our prior co-pending application Ser. No. 172,805 filed July 28, 1980, now abandoned, which in turn is a continuation-in-part of our application Ser. No. 153,117 filed May 27, 1980, now abandoned.

BACKGROUND OF THE INVENTION

1. Field of the Invention

The novel salts of the present invention possess the advantageous antitumor properties of the known parent compound and in addition have unexpectedly high water solubility, thus allowing preparation of useful dosage forms for intravenous administration.

2. Description of the Prior Art

The platinum coordination compound 2-hydroxymalonato diammine platinum (II) having the structure

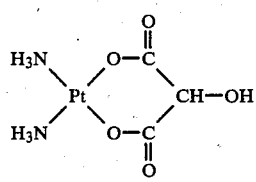

is generically disclosed in U.S. Pat. No. 4,140,707 as an anti-tumor agent. This compound has shown promising activity in a number of animal tumor systems and is presently undergoing further evaluation.

U.S. Pat. No. 4,115,418 discloses the platinum coordination compound 2-hydroxymalonato(1,2-diaminocyclohexane)-platinum (II) of the formula

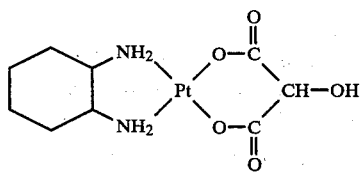

This compound also has shown excellent antitumor activity in preliminary screening and is being subjected to more extensive investigation.

The platinum coordination compound 2-hydroxymalonato (1,1-diaminomethylcyclohexane)-platinum (II) of the formula

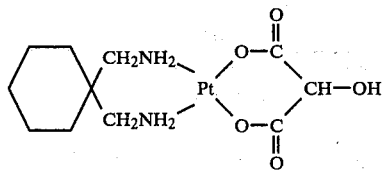

is generically disclosed in U.K. Patent Application No. 2,024,823A as an antitumor agent. Initial screening data indicates that this compound is highly active against L1210 leukemia in mice.

When an antitumor agent such as 2-hydroxymalonato diammine platinum (II), 2-hydroxymalonato (1,2-diaminocyclohexane) platinum (II) or 2-hydroxymalonato (1,1-diaminomethylcyclohexane) platinum (II) is employed for treating mammalian tumors, it is recognized that solubility of the agent is often the controlling factor in determining route or administration and dosage forms. For instance, a water-soluble substance can be generally administered intravenously whereas a water-insoluble material is limited to other forms of parenteral administration such as intramuscular and subcutaneous. A therapeutic agent having water-solubility also facilitates preparation of oral and non-intravenous parenteral dosage forms. Thus, it is decidedly advantageous if a therapeutic agent is water-soluble, particularly when one considers that the most direct route for achieving therapeutic blood levels of a drug is by intravenous administration.

The 2-hydroxymalonato coordination compounds of formulae I-III have very limited solubility in water and thus cannot be used as dosage forms for intravenous administration. Applicants are not aware of any literature disclosing salts of compounds I-III or attempts to prepare water-soluble dosage forms of these compounds for intravenous administration.

It is accordingly an object of the present invention to provide water-soluble, stable, therapeutically acceptable forms of compounds I-III which can be administered intravenously (as well as by other routes). This object as well as other features and advantages of the invention will be readily apparent to those skilled in the art from the disclosure set out below.

SUMMARY OF THE INVENTION

The present invention provides water-soluble salts of 2-hydroxymalonato diammine platinum (II), 2-hydroxymalonato (1,2-diaminocyclohexane) platinum (II) and 2-hydroxymalonato (1,1-diaminomethylcyclohexane) platinum (II) which upon reconstitution with sterile water or a sterile aqueous vehicle can be administered intravenously for treatment of malignant tumors in mammals. More particularly, there are provided the sodium and ammonium salts of 2-hydroxymalonato diammine platinum (II), 2-hydroxymalonato (1,2-diaminocyclohexane) platinum (II) and 2-hydroxymalonato (1,1-diaminomethylcyclohexane) platinum (II).

DETAILED DESCRIPTION

Figure 1:
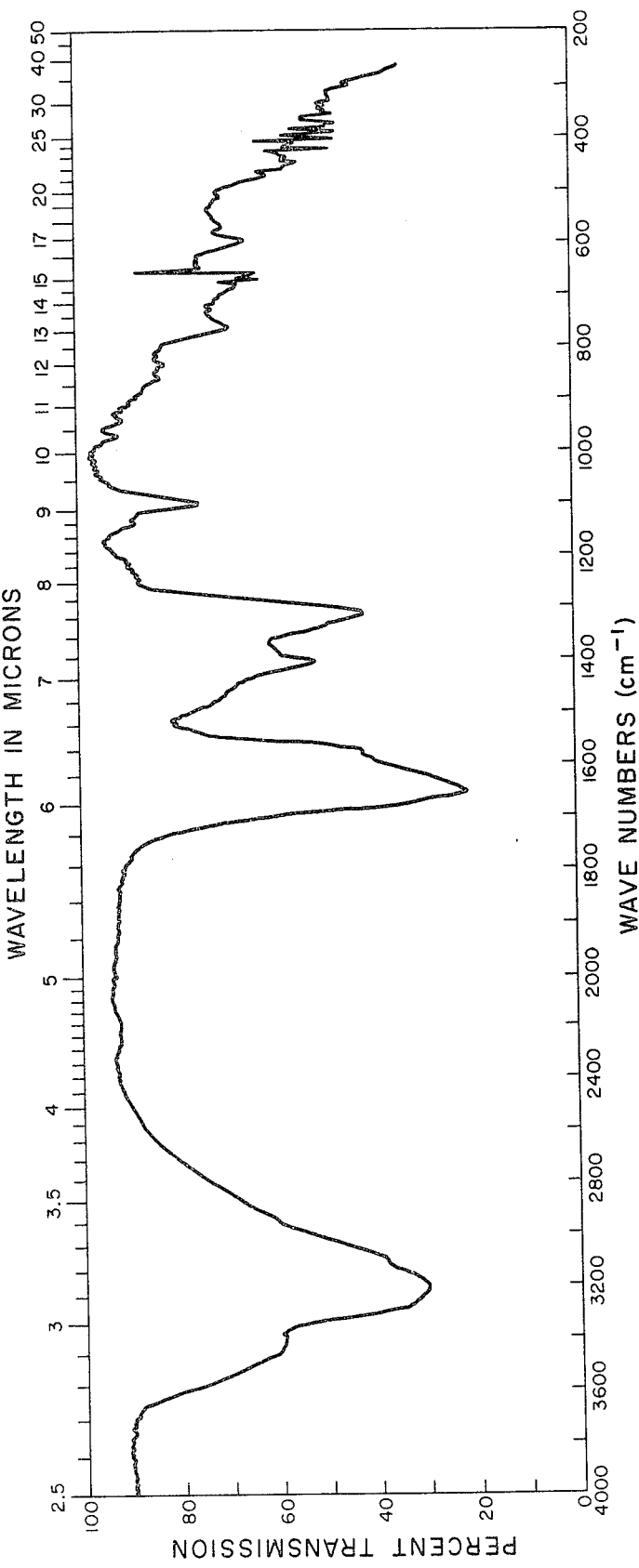
FIG. 1 shows the infrared adsorption spectrum of 2-hydroxymalonato diammine platinum (II), ammonium salt

In investigating the solubility properties of 2-hydroxymalonato diammine platinum (II), 2-hydroxymalonato (1,2-diaminocyclohexane) platinum (II) and 2-hydroxymalonato (1,1-diaminomethylcyclohexane) platinum (II) in various aqueous and non-aqueous solvents, applicants have unexpectedly found that these coordination compounds form both sodium and ammonium salts and that these novel salts possess all of the attributes required for acceptable intravenous dosage forms. The salts provided by the present invention are sufficiently water soluble at room temperature to provide practical intravenous dosage forms. The salts possess good stability both as solids and upon water reconstitution. In nearly all animal tumor models evaluated, the salts when reconstituted with sterile water and administered parenterally exhibited antitumor activity comparable to the parent compound.

Preparation of Salts

The salts of the present invention are prepared by a process which comprises the steps of
(1) providing a suspension of 2-hydroxymalonato-diammine platinum (II), 2-hydroxymalonato-(1,2-diaminocyclohexane)platinum (II) or 2-hydroxymalonato (1,1-diaminomethylcyclohexane) platinum (II) in water;
(2) adding to said suspension with stirring sufficient sodium hydroxide or ammonium hydroxide to form a solution; and
(3) recovering the desired sodium or ammonium salt from said solution.

The 2-hydroxymalonato diammine platinum (II), 2-hydroxymalonato (1,2-diaminocyclohexane)platinum (II) or 2-hydroxymalonato (1,1-diaminomethylcyclohexane)platinum (II) is first slurried or suspended in water. The concentration of the platinum starting material is not critical and may range, for example, between 4 and 70 mg/ml of water. We have found that a suspension containing about 4–7 mg of platinum starting material per ml of water gives good results in preparation of the ammonium salt. Similarly, a 30–40 mg/ml suspension has been found advantageous in preparing the sodium salt. The suspension may be prepared at room temperature or with mild heating (e.g. up to about 60° C.).

To form the sodium salt, about one molar equivalent of sodium hydroxide is then added to the above suspension so as to produce an aqueous solution of the sodium salt. Similarly, at least one molar equivalent and preferably an excess (most preferably about four to five molar equivalents) of ammonium hydroxide is added to produce the ammonium salt in solution. The aqueous mixture of platinum starting material and base is stirred at room temperature or with mild heating (up to about 60° C.) until a solution or near solution of the desired salt is obtained. This solution is then preferably clarified by filtration before recovering the product salt.

The desired sodium or ammonium salt is next recovered from the aqueous solution by conventional procedures such as lyophilization or solvent precipitation. Lyophilization may be carried out in a laboratory or industrial lyophilizer according to methods well-known to those skilled in the art. Solvent precipitation is accomplished by adding to the solution an organic solvent such as acetone or isopropanol in which the desired salt is substantially insoluble (other appropriate antisolvents can be determined by simple test).

Following the recovery step, the product salt may be optionally subjected to purification as by washing with an organic solvent in which the salt is substantially insoluble (e.g. acetone or isopropanol) and then drying.

The salts of the present invention may be obtained in the form of hydrates or solvates with organic solvents as well as in the anhydrous or solvent-free state. All such hydrates and solvates are thus intended to be included within the scope of the invention.

Structural Studies

There exist two possibilities for the structure of the 2-hydroxymalonato salts of the present invention, i.e.

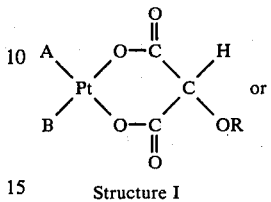

Structure I

Structure II wherein A and B each represent $H_3N$ or when taken together with the Pt represent

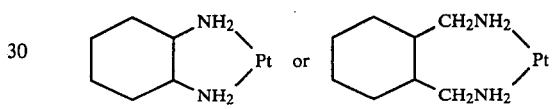

and R represents Na or $NH_4$. $^{13}C$-NMR studies have determined that structure I is the correct structure.

The proof for structure I is based on the presence of the methine carbon

in the carbon-13 spectrum of each of the sodium salts. Structure II has no such methine carbon and hence cannot represent the correct structure of the salts.

Biological Properties

The sodium and ammonium salts of the present invention were tested against transplantable mouse tumors as indicated below. The methodology used generally followed the protocols of the National Cancer Institute (*Cancer Chemotherapy Rep.*, Part 3, 3, 1–103 (1972). The essential experimental details are given at the bottom of the following tables.

L1210 Leukemia—Test 1

TABLE 1

| | | | | | | |
|---|---|---|---|---|---|---|
| Material | Dose, Route mg/ kg/ day | Treatment Schedule | MST Days | Effect MST % T/C | Average Weight Change | Survivors Day 5 (30) |
| Cis-DDP (in saline) | 10, (ip) | d. 1 only | 14.5 | 207 | −3.6 | 6/6 |
| | 8 | | 13.5 | 193 | −4.1 | 6/6 |
| | 6 | | 13.0 | 186 | −2.8 | 6/6 |
| | 4 | | 11.5 | 164 | −0.7 | 6/6 |

TABLE 1-continued

Effect of Ammonium Salt of 2-Hydroxymalonato Diammine Platinum (II) on L1210 Leukemia

| Material | Dose, Route mg/ kg/ day | Treatment Schedule | MST Days | Effect MST % T/C | Average Weight Change | Survivors Day 5 (30) |
|---|---|---|---|---|---|---|
| | 2 | qd 1 → 9 | 17.5 | 250 | −3.3 | 6/6 |
| | 1 | | 10.5 | 150 | −0.9 | 6/6 |
| | 0.5 | | 7.0 | 100 | +1.5 | 6/6 |
| | 0.025 | | 8.5 | 121 | +3.6 | 6/6 |
| Cis-DDP (in H₂O) | 10, (ip) | d. 1 only | TOX | TOX | TOX | 1/6 |
| | 8 | | TOX | TOX | TOX | 4/6 |
| | 6 | | TOX | TOX | TOX | 1/6 |
| | 4 | | 7.0 | 100 | −5.9 | 6/6 |
| | 2 | qd 1 → 9 | 6.0 | 86 | −4.0 | 4/6 |
| | 1 | | 8.0 | 114 | −3.7 | 6/6 |
| | 0.5 | | 10.0 | 143 | −3.8 | 6/6 |
| | 0.25 | | 11.0 | 157 | −1.4 | 5/6 |
| 2-Hydroxy- malonato diammine platinum (II) | 80, (ip) | d. 1 only | 12.0 | 171 | −2.9 | 6/6 |
| | 60 | | 11.0 | 157 | −1.9 | 5/6 |
| | 40 | | 10.0 | 143 | −1.7 | 6/6 |
| | 20 | | 10.0 | 143 | −0.5 | 6/6 |
| 2-Hydroxy- malonato diammine platinum (II), Ammonium salt | 100, (ip) | d. 1 only | 11.5 | 164 | −3.3 | 4/6 |
| | 80 | | 11.0 | 157 | −2.6 | 6/6 |
| | 60 | | 11.0 | 157 | −2.2 | 6/6 |
| | 40 | | 10.0 | 143 | −1.2 | 6/6 |
| | 20 | | 9.0 | 129 | +0.1 | 6/6 |
| | 10 | | 9.5 | 136 | +0.6 | 6/6 |
| Control | Saline | | 7.0 | — | +1.9 | 10/10 |

Tumor inoculum: 10⁶ ascites cells implanted ip
Host: BDF₁ ♀ mice.
Tox: <4/6 mice alive on Day 5.
Evaluation: MST = median survival time.
Effect: % T/C = (MST treated/MST control) × 100.
Criteria: % T/C ≧ 125 considered significant antitumor activity.
cis-DDP: cis-diammine dichloroplatinum (II)

This evaluation of the ammonium salt finds the drug to be active against L1210 (ip) leukemia when administered ip one day post-implant of 10⁶ L1210 cells (maximum T/C was 164%). The salt was comparable to the insoluble parent compound in terms of potency and antileukemic activity but inferior in both respects to cis-diammine dichloroplatinum (II) (in saline). The vehicle for the ammonium salt was water.

B. L1210 Leukemia—Test 2

TABLE 2

Effect of Sodium Salt of 2-hydroxymalonato Diammine Platinum (II) on L1210 Leukemia

| Material (Route) | Treatment Schedule | Dose mg/ kg/ inj | MST Days | Effect MST % T/C | Average Weight Change, g | Survivors Day 5 (30) |
|---|---|---|---|---|---|---|
| Cis-DDP (ip) | d. 1 | 10 | 15.0 | 214 | −4.4 | 6/6 |
| | | 8 | 13.0 | 186 | −2.8 | 6/6 |
| | | 6 | 12.0 | 171 | −1.8 | 6/6 |
| | | 4 | 9.5 | 136 | −0.7 | 6/6 |
| | qd 1 → 9 | 2.4 | 15.0 | 214 | −3.3 | 6/6 |
| | | 1.6 | 11.0 | 157 | −2.2 | 6/6 |
| | | 0.8 | 7.5 | 107 | −0.7 | 6/6 |
| | | 0.4 | 7.0 | 100 | +1.6 | 6/6 |
| (iv) | d. 1 | 10 | 10.0 | 143 | −3.9 | 6/6 |
| | | 8 | 9.0 | 129 | −3.7 | 6/6 |
| | | 6 | 8.0 | 114 | −0.2 | 6/6 |
| | | 4 | 7.0 | 100 | +1.8 | 6/6 |
| | d. 1, 5 & 9 | 8 | 12.5 | 179 | −2.1 | 6/6 |
| | | 6 | 11.5 | 164 | −1.1 | 6/6 |
| | | 4 | 7.0 | 100 | +0.8 | 6/6 |
| | | 2 | 7.0 | 100 | +1.7 | 6/6 |
| 2-Hydroxy- malonato diammine platinum | d. 1 | 120 | 9.5 | 136 | −3.4 | 6/6 |
| | | 90 | 10.0 | 143 | −2.8 | 6/6 |
| | | 60 | 8.5 | 121 | −0.7 | 6/6 |
| | | 40 | 8.0 | 114 | −0.3 | 6/6 |
| (II), Sodium salt (ip) | qd 1 → 9 | 24 | 14.5 | 207 | −3.8 | 6/6 |
| | | 16 | 11.0 | 157 | −1.8 | 6/6 |
| | | 8 | 8.0 | 114 | +0.7 | 6/6 |
| | | 4 | 7.0 | 100 | +1.8 | 6/6 |
| (iv) | d. 1 | 120 | 7.0 | 100 | +1.8 | 6/6 |
| | | 90 | 7.5 | 107 | +1.2 | 6/6 |
| | | 60 | 7.0 | 100 | +1.3 | 5/5 |
| | | 40 | 7.0 | 100 | +2.3 | 6/6 |
| | d. 1, 5 & 9 | 80 | 7.0 | 100 | −0.3 | 6/6 |
| | | 60 | 10.0 | 143 | +0.8 | 6/6 |
| | | 40 | 7.5 | 107 | +2.1 | 6/6 |
| | | 20 | 7.0 | 100 | +2.0 | 6/6 |
| Control | Saline | | 7.0 | — | +2.2 | 10/10 |

Tumor inoculum: 10⁶ ascites cells implanted i.p.
Host: BDF₁ ♀ mice.
Evaluation: MST = median survival time.
Effect: % T/C = (MST treated/MST control) × 100.
Criteria: % T/C ≧ 125 considered significant antitumor activity.

Although single ip doses of the sodium salt were not as effective against ip L1210 as were single doses of cis-diamminedichloroplatinum (II) (maximum T/C of 143% vs. 214%, respectively), multi-dose therapy with each drug given ip (qd 1→9) resulted in similar increases in lifespan (maximum T/C of 207–214%). Intravenous administration of sodium salt was effective only when given on a multi-dose regimen (T/C of 143%) and was not as effective as when given ip or when compared to iv cis-diamminedichloroplatinum (II) (maximum T/C of 179%) on the same multi-dose schedule.

C. L1210 Leukemia—Test 3

TABLE III

Effect of 2-Hydroxymalonato Diammine Platinum (II) Salts on L1210 Leukemia

| Material (Vehicle) | Dose, (ip) mg/kg | MST Days | Effect MST % T/C | Average Weight Change | Survivor Day 5 |
|---|---|---|---|---|---|
| Cis-DDP (Saline) | 10 | 10.5 | 150 | −4.5 | 6/6 |
| | 8 | 10.5 | 150 | −1.8 | 6/6 |
| | 6 | 10.0 | 143 | −2.3 | 6/6 |
| | 4 | 10.0 | 143 | −1.7 | 6/6 |
| 2-Hydroxymalonato diammine platinum (II) (CMC + saline) | 100 | 7.0 | 100 | −4.6 | 6/6 |
| | 80 | 9.0 | 129 | −3.5 | 6/6 |
| | 60 | 10.0 | 143 | −2.9 | 6/6 |
| | 40 | 8.0 | 114 | −1.7 | 6/6 |
| 2-Hydroxymalonato diammine platinum (II), NH₄⁺ salt (H₂O) | 100 | 7.5 | 107 | −0.6 | 6/6 |
| | 80 | 10.0 | 143 | −2.8 | 6/6 |
| | 60 | 10.0 | 143 | −1.7 | 6/6 |
| | 40 | 10.0 | 143 | −1.4 | 6/6 |
| 2-Hydroxymalonato diammine platinum (II), NH₄⁺ salt (Saline) | 100 | 10.0 | 143 | −1.6 | 6/6 |
| | 80 | 8.0 | 114 | −0.8 | 6/6 |
| | 60 | 7.0 | 100 | +1.6 | 6/6 |
| | 40 | 8.0 | 114 | +1.7 | 6/6 |
| 2-Hydroxymalonato diammine platinum (II), sodium salt (H₂O) | 100 | 10.0 | 143 | −3.3 | 6/6 |
| | 80 | 10.0 | 143 | −3.9 | 6/6 |
| | 60 | 10.0 | 143 | −2.3 | 6/6 |
| | 40 | 9.0 | 129 | −1.6 | 6/6 |
| | 20 | 10.0 | 143 | +0.4 | 6/6 |
| | 10 | 8.0 | 114 | +0.5 | 6/6 |
| 2-Hydroxymalonato diammine platinum (II), sodium salt (Saline) | 100 | 9.0 | 129 | −2.8 | 6/6 |
| | 80 | 10.0 | 143 | −1.8 | 6/6 |
| | 60 | 8.0 | 114 | −0.1 | 6/6 |
| | 40 | 8.0 | 114 | −0.7 | 6/6 |
| | 20 | 7.0 | 100 | +1.5 | 6/6 |
| | 10 | 7.0 | 100 | +2.1 | 6/6 |

TABLE III-continued
Effect of 2-Hydroxymalonato Diammine Platinum (II) Salts on L1210 Leukemia

| Material (Vehicle) | Dose, (ip) mg/kg | MST Days | Effect MST % T/C | Average Weight Change | Survivor Day 5 |
|---|---|---|---|---|---|
| Control | Saline | 7.0 | — | +1.8 | 10/10 |

Tumor inoculum: $10^6$ ascites cells implanted i.p.
Host: $BDF_1$ ♀ mice.
Treatment: Day 1 only
Evaluation: MST = median survival time.
Effect: % T/C = (MST treated/MST control) × 100.
Criteria: % T/C ≧ 125 considered significant antitumor activity.
CMC: Caraboxymethyl cellulose Maximum increase in median lifespan caused by the ammonium and sodium salts (T/C of 143% for each drug) were not different when saline and water were compared as vehicles; however, the use of saline severely limited the range of doses over which the maximal antileukemic effect was obtained for both salts, i.e. water is thus the preferred vehicle. Also, in this study, all of the forms of 2-hydroxymalonato diammine platinum (II) behaved comparable to cis-diamminedichloroplatinum (II) with regard to maximum antileukemic effect obtained following single dose therapy.

D. B16 Melanoma—Test 1
TABLE IV
Effect of Ammonium Salt of 2-Hydroxymalonato Diammine Platinum (II) on B16 Melanoma

| Material (Vehicle) | Dose, (ip) mg/kg/day | MST Days | Effect MST % T/C | Av. Wt. Change, g Day 5 | Survivors Day 5 (60) |
|---|---|---|---|---|---|
| Cis-DDP (Saline) | 2.0 | 7.0 | 36 | −4.5 | 8/10 |
|  | 1.6 | 7.0 | 36 | −4.3 | 9/9 |
|  | 0.8 | 34.0 | 174 | −1.0 | 10/10 |
| 2-Hydroxymalonato diammine platinum (II) (CMC + H₂O) | 32 | 7.5 | 38 | −3.8 | 10/10 |
|  | 24 | 10.5 | 54 | −3.3 | 8/9(1) |
|  | 16 | >60.0* | >308* | −3.0 | 10/10(5)* |
|  | 8 | 34.5 | 177 | −1.9 | 10/10 |
|  | 4 | 36.5 | 187 | −1.2 | 10/10(2) |
|  | 2 | 26.0 | 133 | −0.6 | 10/10 |
| 2-Hydroxymalonato diammine platinum (II), NH₄⁺ salt (H₂O) | 32 | 6.0 | 31 | −3.5 | 5/10 |
|  | 24 | 7.0 | 36 | −3.8 | 10/10 |
|  | 16 | 23.5 | 121 | −3.0 | 8/10(1) |
|  | 8 | 37.0 | 190 | −1.9 | 10/10(1) |
|  | 4 | 37.5 | 192 | −1.0 | 10/10 |
| Control | Saline | 19.5 | — | −0.2 | 10/10 |

Tumor inoculum: 0.5 ml of a 10% tumor brei.
Host: $BDF_1$ ♂ mice.
Treatment: QD 1 → 9
Evaluation: MST = median survival time.
Effect: % T/C = (MST treated/MST control) × 100.
Criteria: % T/C ≧ 125 considered significant antitumor activity.
*One of the 5 mice alive on Day 60 had a tumor. MST of dying mice only was 53 days (T/C: 272%).

The ammonia salt was slightly more effective than cis-diamminedichloroplatinum (II) (maximum T/C of 190% with 1 of 10 mice curved vs. T/C of 174% with no cures, respectively) against tip B16 but not as good as insoluble 2-hydroxymalonato diammine platinum (II) (T/C>308%, 4/10 cures).

E. B16 Melanoma—Test 2
TABLE V
Effect of 2-Hydroxymalonato Diammine Platinum (II) Salts on B16 Melanoma

| Material | Dose, (ip) mg/kg/day | MST Days | Effect MST % T/C | Average Weight Change, g | Survivors Day 10 (60) |
|---|---|---|---|---|---|
| Cis-DDP | 1.6 | 35.5 | 173 | −2.7 | 10/10 |
|  | 0.8 | 28.5 | 139 | −1.5 | 10/10 |
|  | 0.4 | 25.0 | 121 | −2.0 | 8/10 |
| 2-Hydroxymalonato diammine platinum (II) | 16 | >60.0ᵃ | >293ᵃ | −2.3 | 9/10(7)ᵇ |
|  | 8 | 39.0 | 190 | −2.1 | 10/10(1) |
|  | 4 | 33.5 | 163 | −1.1 | 10/10 |
|  | 2 | 37.5 | 182 | −1.1 | 10/10(1) |
| 2-Hydroxymalonato diammine platinum (II), (NH₄⁺) | 16 | 48.0 | 234 | −1.3 | 8/10(2)ᶜ |
|  | 8 | 37.0 | 180 | −0.9 | 9/10 |
|  | 4 | 32.5 | 158 | −2.0 | 9/10 |
|  | 2 | 31.5 | 153 | −0.7 | 9/10 |
| 2-Hydroxymalonato diammine platinum (II), (Na⁺) | 16 | 38.0 | 185 | −2.9 | 10/10(1)ᵈ |
|  | 8 | 33.5 | 163 | −3.2 | 9/10 |
|  | 4 | 34.5 | 168 | −2.8 | 10/10 |
|  | 2 | 33.0 | 160 | −1.5 | 10/10 |
| Control | Saline | 20.5 | — | −0.7 | 9/9 |

Tumor inoculum: 0.5 ml of a 10% tumor brei.
Host: $BDF_1$ ♂ mice.
Treatment: QD 1 → 9
Evaluation: MST = median survival time.
Effect: % T/C = (MST treated/MST control) × 100.
Criteria: % T/C ≧ 125 considered significant antitumor activity.
*One of the 5 mice alive on Day 60 had a tumor. MST of dying mice only was 53 days (T/C: 272%).
ᵃMST (% T/C) of dying mice only; not including toxic death: 41.5 days (202%)
ᵇOnly 3 of the 7 mice were tumor-free at autopsy (as determined by visual inspection).
ᶜOnly 1 of the 2 mice were tumor-free at autopsy.
ᵈTumor found at autopsy.

Again in this experiment the ammonium salt was slightly more effective than cis-diamminedichloroplatinum (II) but not as effective as the parent insoluble compound. The sodium salt was not as effective as the ammonium salt and was comparable or only slightly better than cis-diamminedichloroplatinum (II) vs. ip B16.

F. B16 Melanoma—Test 3
TABLE VI
Effect of Sodium Salt of 2-Hydroxymalonato Diammine Platinum (II) on B16 Melanoma

| Material (Route) | Dose, mg/kg/inj | Treatment Schedule | MST Days | Effect MST % T/C | Average Weight Change, g | Survivors Day 10 (60) |
|---|---|---|---|---|---|---|
| Cis-DDP (ip) | 2.4 | qd 1 → 9 | 29.5 | 97 | −3.5 | 10/10 |
|  | 1.6 |  | 36.0 | 118 | −2.4 | 10/10 |
|  | 0.8 |  | 34.5 | 113 | −0.4 | 10/10 |
| (iv) | 8 | d. 1, 5 & 9 | 38.0 | 125 | −2.8 | 9/10 |
|  | 6 |  | 40.0 | 131 | −2.2 | 10/10 |
|  | 4 |  | 47.5 | 156 | −0.6 | 10/10 |
| 2-Hydroxymalonato diammine platinum (II) Sodium salt (ip) | 24 | qd 1 → 9 | TOX | TOX | −3.5 | 5/10 |
|  | 16 |  | 38.0 | 125 | −2.7 | 9/10 |
|  | 12 |  | 28.0 | 92 | −2.3 | 9/10 |
|  | 8 |  | 31.0 | 102 | −1.0 | 10/10 |
| (iv) | 100 | d. 1, 5 & 9 | TOX | TOX | −3.4 | 3/10 |
|  | 80 |  | TOX | TOX | −1.5 | 4/8 |
|  | 60 |  | 33.0 | 108 | −1.6 | 7/10 |
|  | 40 |  | 33.0 | 108 | +0.7 | 8/10 |
|  | 20 |  | 28.5 | 93 | +0.5 | 10/10 |
| 2-Hydroxymalonato diammine platinum | 24 | qd 1 → 9 | TOX | TOX | −4.1 | 4/10 |
|  | 16 |  | 14.5 | 48 | −3.9 | 10/10 |
|  | 12 |  | 35.0 | 115 | −3.3 | 9/9 |
|  | 8 |  | 40.0 | 131 | −1.4 | 9/10 |

TABLE VI-continued
Effect of Sodium Salt of 2-Hydroxymalonato Diammine Platinum (II) on B16 Melanoma

| Material (Route) | Treatment Schedule | Dose, mg/kg/inj | MST Days | Effect MST % T/C | Average Weight Change, g | Survivors Day 10 (60) |
|---|---|---|---|---|---|---|
| (II) (ip) | | | | | | |
| Control | Saline | | 30.5 | — | +1.1 | 10/10 |

Tumor inoculum: Trocar fragments, sc.
Host: BDF$_1$ ♂ mice.
Tox: < 7/10 alive on Day 10.
Evaluation: MST = median survival time.
Effect: % T/C = (MST treated/MST control) × 100.
Criteria: % T/C ≧ 125 considered significant antitumor activity.

Against sc-implanted B16 melanoma, ip cis-diamminedichloroplatinum (II) was inactive and iv cis-diamminedichloroplatinum (II) showed mild activity (maximum T/C of 156%). The sodium salt given ip displayed borderline activity (T/C of 125%) but was not active by the iv route. The insoluble 2-hydroxymalonato diammineplatinum (II) given ip also had weak activity T/C of 131%).

G. Lewis Lung Carcinoma—Test 1

TABLE VII
Effect of Sodium Salt of 2-Hydroxymalonato Diammine Platinum (II) on Lewis Lung Carcinoma

| Material Route | Treatment Schedule | Dose mg/kg/inj | MST Days | Effect MST % T/C | Av. Wt. Change, g Day 9 | Survivors Day 9 (48) |
|---|---|---|---|---|---|---|
| Cis DDP (ip) | qd 5 → 13 | 2.4 | 26.5 | 212 | −2.4 | 6/6 |
| | | 1.6 | 23.0 | 184 | −1.8 | 6/6 |
| | | 0.8 | 17.0 | 136 | −0.6 | 5/6 |
| | | 0.4 | 15.5 | 124 | −0.4 | 6/6 |
| (ip) | d. 5, 9 & 13 | 8 | 16.0 | 128 | −2.8 | 6/6 |
| | | 6 | 27.5 | 220 | −0.8 | 6/6 |
| | | 4 | 21.0 | 168 | −0.3 | 6/6 |
| | | 2 | 19.0 | 152 | +0.8 | 6/6 |
| (iv) | d. 5, 9 & 13 | 8 | 14.0 | 112 | −0.7 | 6/6 |
| | | 6 | 13.5 | 108 | −1.1 | 6/6 |
| | | 4 | 15.0 | 120 | −0.7 | 6/6 |
| | | 2 | 13.0 | 104 | +0.6 | 6/6 |
| 2-Hydroxymalonato diammine platinum (II) (ip) | qd 5 → 13 | 24 | 27.5 | 220 | −0.9 | 6/6 |
| | | 16 | 22.0 | 176 | −2.1 | 6/6 |
| | | 12 | 21.0 | 168 | −0.8 | 6/6 |
| | | 8 | 14.0 | 112 | −0.9 | 6/6 |
| (ip) | d. 5, 9 & 13 | 80 | 19.0 | 152 | +0.2 | 6/6 |
| | | 60 | 19.5 | 156 | +0.7 | 6/6(1) |
| | | 40 | 15.0 | 120 | +0.6 | 6/6 |
| | | 20 | 12.5 | 100 | +0.4 | 6/6 |
| 2-Hydroxymalonato diammine platinum (II) Sodium salt (ip) | qd 5 → 13 | 16 | 20.0 | 160 | −1.8 | 6/6 |
| | | 12 | 18.5 | 148 | −0.9 | 6/6 |
| | | 8 | 17.5 | 140 | −0.5 | 6/6 |
| | | 4 | 15.0 | 120 | 0 | 5/6 |
| (ip) | d. 5, 9 & 13 | 80 | 33.5 | 268 | −1.8 | 6/6(2) |
| | | 60 | 24.5 | 196 | −1.2 | 6/6(1) |
| | | 40 | 18.5 | 148 | −0.5 | 6/6(1) |
| | | 20 | 15.5 | 124 | +1.0 | 6/6 |
| (iv) | d. 5, 9 & 13 | 80 | 18.5 | 148 | −0.2 | 6/6 |
| | | 60 | 16.5 | 132 | +0.9 | 6/6 |
| | | 40 | 13.5 | 108 | +0.5 | 6/6 |
| | | 20 | 12.5 | 100 | +0.6 | 6/6 |
| Control | Saline | | 12.5 | — | +1.7 | 10/10 |

Tumor inoculum: 10$^5$ LL cells, ip
Host: BDF$_1$ ♂ mice.
Tox: < 4/6 survivors Day 5.
Evaluation: MST = median survival time.
Effect: % T/C = (MST treated/MST control) × 100.
Criteria: % T/C ≧ 125 considered significant antitumor activity.

Delayed initiation of therapy (day 5) of mice implanted ip with Lewis lung carcinoma (10$^5$ cells) found ip diammine dichloroplatinum (II) to be quite effective (maximum T/C of 212–220%) but iv-cis-DDP to be inactive. Intraperitoneal administration of 2-hydroxymalonato diammine platinum (II) gave an optimal effect (maximum T/C of 220%) comparable to cis-DDP. The sodium salt gaven ip yielded a maximum T/C of 268% with 2 to 6 long-term survivors (day 48) and the sodium salt given iv yielded a positive result of a 148% T/C.

H. L-1210 Leukemia

TABLE VIII
Effect of Sodium Salt of 2-Hydroxymalonato(1,2-diaminocyclohexane)platinum (II) on L-1210 Leukemia

| Material | Treatment Schedule | Dose, ip mg/kg/inj | MST Days | Effect MST % T/C | Average Weight Change, g | Survivors Day 5 (30) |
|---|---|---|---|---|---|---|
| Cis-DDP | d. 1 | 10 | 12.5 | 208 | −2.0 | 6/6 |
| | | 8 | 9.5 | 158 | −2.8 | 6/6 |
| | | 6 | 10.0 | 167 | −3.7 | 6/6 |
| | | 4 | 10.0 | 167 | −1.5 | 6/6 |
| | qd 1 → 9 | 2.4 | 10.0 | 167 | −3.1 | 6/6 |
| | | 1.6 | 12.0 | 200 | −2.5 | 6/6 |
| | | 0.8 | 8.0 | 133 | −0.8 | 6/6 |
| | | 0.4 | 7.0 | 117 | +0.8 | 6/6 |
| 2-Hydroxymalonato-(1,2-diaminocyclohexane)-platinum (II) | d. 1 | 200 | TOX | TOX | TOX | 0/6 |
| | | 100 | 11.0 | 183 | −1.5 | 6/6 |
| | | 50 | 9.0 | 150 | +0.1 | 6/6 |
| | | 25 | 8.5 | 142 | −0.3 | 6/6 |
| 2-Hydroxymalonato-(1,2-diaminocyclohexane)-platinum (II), sodium salt | d. 1 | 200 | TOX | TOX | TOX | 1/6 |
| | | 100 | 13.0 | 217 | +2.6 | 6/6 |
| | | 50 | 12.5 | 208 | −1.2 | 6/6 |
| | | 25 | 11.0 | 183 | −0.8 | 6/6 |
| | qd 1 → 9 | 48 | 6.0 | 100 | −3.3 | 5/6 |
| | | 24 | 20.5 | 342 | −2.4 | 4/6 |
| | | 12 | 14.0 | 233 | −2.3 | 6/6 |
| | | 6 | 11.5 | 192 | −0.9 | 6/6 |
| Control | Saline | | 6.0 | — | +1.2 | 10/10 |

Tumor inoculum: 10$^6$ ascites cells implanted i.p.
Host: CDF$_1$ ♀ mice.
Tox: < 4/6 mice alive on day 5.
Evaluation: MST = median survival time.
Effect: % T/C = (MST treated/MST control) × 100.
Criteria: % T/C ≧ 125 considered significant antitumor activity.

Following single ip injections of cis-diamminedichloroplatinum (II), 2-hydroxymalonato(1,2-diaminocyclohexane)platinum (II) and 2-hydroxymalonato(1,2-diaminocyclohexane)platinum (II), sodium salt, maximum T/C values of 208%, 183% and 217%, respectively, were obtained indicating each agent was active against L-1210 leukemia. The optimal doses at which these effects were observed are as follows: cis-diamminedichloroplatinum (II)—10 mg/kg; 2-hydroxymalonato(1,2-diaminocyclohexane)platinum (II)—100 mg/kg; 2-hydroxymalonato(1,2-diaminocyclohexane)platinum (II), sodium salt—100 mg/kg. The latter two drugs were also evaluated at 200 mg/kg and this dose was lethal for both of them. In addition, cis-diamminedichloroplatinum (II) was compared to the sodium salt of 2-hydroxymalonato(1,2-diaminocyclohexane)platinum (II) using a qd 1→9 dosing regimen. Cis-diamminedichloroplatinum (II) caused a maximum T/C of 200% at 1.6 mg/kg/inj. In comparison, the 2-hydroxymalonato(1,2-diaminocyclohexane)platinum (II), sodium salt, caused a T/C of 342% at 24 mg/kg/injection and 233% at 12 mg/kg/inj.

Based on the above test the sodium salt of 2-hydroxymalonato(1,2-diaminocyclohexane)platinum (II) has comparable or greater activity against L-1210 leukemia than both the insoluble parent compound from which it was derived and cis-diamminedichloroplatinum (II). The sodium salt and parent compound appear to have comparable potency.

I. L-1210 Leukemia

TABLE IX

Effect of Sodium Salt of 2-Hydroxymalonato(1,1-diaminomethylcyclohexane)platinum (II) on L-1210 Leukemia

| Material (vehicle) | Treatment Schedule | Dose, ip mg/kg/inj | MST Days | Effect MST % T/C | Average Weight Change, g | Survivors Day 5 (45) |
|---|---|---|---|---|---|---|
| Cis-DDP | Day 1 | 8 | 12.0 | 185 | −3.4 | 6/6 |
| | | 6 | 10.0 | 154 | −3.7 | 6/6 |
| | | 4 | 8.0 | 123 | −2.1 | 6/6 |
| | | 2 | 9.0 | 138 | −0.7 | 6/6 |
| | qd 1→9 | 2.4 | 11.5 | 177 | −3.8 | 6/6 |
| | | 1.6 | 10.0 | 154 | −2.9 | 6/6 |
| | | 0.8 | 9.0 | 138 | −2.1 | 6/6 |
| | | 0.4 | 7.0 | 108 | −0.6 | 6/6 |
| 2-Hydroxymalonato (1,1-diaminomethylcyclohexane)platinum (II) (CMC + H$_2$O) | Day 1 | 36 | 16.0 | 246 | −3.6 | 5/6 |
| | | 24 | 14.5 | 223 | −2.8 | 6/6 |
| | | 18 | 11.5 | 169 | −2.0 | 6/6 |
| | | 12 | 12.0 | 185 | −1.6 | 6/6 |
| | qd 1→9 | 12 | 17.5 | 269 | −2.1 | 6/6 |
| | | 8 | 17.5 | 269 | −2.1 | 6/6 |
| | | 4 | 12.5 | 192 | −1.7 | 6/6 |
| | | 2 | 9.0 | 138 | −1.3 | 6/6 |
| 2-Hydroxymalonato (1,1-diaminomethylcyclohexane)platinum (II), sodium salt (H$_2$O) | Day 1 | 48 | 13.0 | 200 | −3.6 | 6/6 |
| | | 36 | 14.5 | 223 | −4.3 | 6/6 |
| | | 24 | 14.0 | 215 | −3.7 | 6/6 |
| | | 12 | 10.5 | 162 | −1.8 | 6/6 |
| | qd 1→9 | 12 | 19.0 | 292 | −3.0 | 6/6 |
| | | 8 | 15.5 | 238 | −1.3 | 6/6 |
| | | 4 | 10.0 | 154 | −1.2 | 6/6 |
| | | 2 | 8.5 | 131 | −1.3 | 6/6 |
| Control | Saline | | 6.5 | — | +1.0 | 10/10 |

Tumor inoculum: 10$^6$ ascites cells implanted ip.
Host: CDF$_1$ ♀ mice.
Tox: < 4/6 mice alive on Day 5.
Evaluation: MST = median survival time.
Effect: % T/C = (MST treated/MST control) × 100.
Criteria: % T/C ≧ 125 considered significant antitumor activity
CMC: carboxymethyl cellulose.

Table IX indicates that both 2-hydroxymalonato(1,1-diaminomethylcyclohexane)platinum (II) and its sodium salt were more active than cis-diamminedichloroplatinum (II) against L-1210 leukemia in mice. Following single ip injection of each platinum compound, maximum T/C values, obtained at what are considered to be maximum tolerated doses, were as follows: 185% for cis-diamminedichloroplatinum (II) at 8 mg/kg, 246% for 2-hydroxymalonato (1,1-diaminomethylcyclohexane)-platinum (II) at 36 mg/kg and 223% for the sodium salt of 2-hydroxymalonato (1,1-diaminocyclohexane)-platinum (II) at 36 mg/kg.

Similarly, following qd 1→9 dosing, maximum T/C values achieved were: 177% for cis-diamminedichloroplatinum (II) at 2.4 mg/kg/injection, 269% for 2-hydroxymalonato (1,1-diaminomethylcyclohexane)-platinum (II) at both 8 and 12 mg/kg/injection and 292% for 2-hydroxymalonato (1,1-diaminomethylcyclohexane)platinum (II), sodium salt, at 12 mg/kg/injection. Based on the above data, the water soluble sodium salt of 2-hydroxymalonato (1,1-diaminomethylcyclohexane)platinum (II) appears to be as active and as potent vs. L-1210 leukemia in mice as the water-insoluble parent compound.

As illustrated by the above experiments, the salts of the present invention exhibit inhibitory action aginst malignant tumors in mammals. For administration by the parenteral route, they are preferably dissolved in water.

The salts are preferably administered parenterally to a mammal afflicted with a malignant tumor. The duration of treatment and the dose level will, of course, depend on the size of the host animal, nature and size of the tumor, etc. Generally, however, a single dose of about 80 mg/kg will be sufficient. When given in multiple doses, suitable dosage regimens include 60–80 mg/kg per injection every fourth day for a total of three injections, 20 mg/kg per injection once a day for 4 days and 16 mg/kg per injection once a day for 9 days.

The following examples are provided for illustrative purposes only and are not intended to limit the scope of the invention.

EXAMPLE 1

2-Hydroxymalonato diammine platinum (II), ammonium salt

To a slurry of 2-hydroxymalonato diammine platinum (II) (650 mg) in 100 ml water, there was added 1 ml of concentrated NH$_4$OH. The reaction mixture was slurried in the dark at 22° C. for 24 hours and a pH 10.7 solution or near solution was obtained. The solution was passed through a 0.45 micron Millipore (Millipore Corporation) filter, 1 inch diameter, to effect clarification. The filtrate was then lyophilized in a 500 ml round-bottom flask for 24 hours to yield 550 mg of title product.

Properties: Water-solubility at room temperature = 10 mg/ml IR(KBr): absorption peaks at 3200, 3400 (OH, NH) and 1640 (strong NH$_4^+$)

Analysis Calc'd for C$_3$H$_7$N$_2$O$_5$Pt.NH$_4$.H$_2$O: C, 9.8; H, 3.1; N, 11.0. Found: C, 9.77; H, 3.14; N, 11.14. % H$_2$O (KF)=3.37
UV(H$_2$O): λ$_{max}$=204; A=1.54; a=14.3

EXAMPLE 2

2-Hydroxymalonato diammine platinum (II), ammonium salt

To a slurry of 2-hydroxymalonato diammine platinum (II) (2 g) in 400 ml of sterile water at room temperature (22°–25° C.), there was added 3.5 ml of concentrated NH$_4$OH. The reaction mixture was stirred vigorously for 6 hours to give a pH 10.7 solution. The solution was passed through a 0.45 micron Millipore filter to remove particles and lint. The filtrate was then lyophilized for 24 hours to give the title salt.

Properties: Water-solubility at 22°–25° C. = 10 mg/ml IR(KBr): as shown in FIG. 1
Analysis Calc'd for C$_3$H$_7$N$_2$O$_5$Pt.NH$_4$.H$_2$O: C, 9.8; H, 3.1; N, 11.0. Found: C, 9.97; N, 3.11; N, 10.90. % H$_2$O (KF)=4.07
UV (1.13 mg in 10 ml H$_2$O): λ$_{max}$=2.05; A=1.62; a=14.3

EXAMPLE 3

2-Hydroxymalonato diammine platinum (II), sodium salt

To a slurry of 2-hydroxymalonato diammine platinum (II) (245 mg) in 15 ml sterile water, there was added with stirring 0.8 ml of 1 N NaOH. The mixture was heated to 50° C., and a pH 10.4 solution was obtained. The solution was cooled to 25° C. and lyophilized for 24 hours to give the title salt as a fluffy powder. Properties:

Analysis Calc'd for $C_3H_7N_2O_5Pt.Na$ C, 9.2; H, 2.16; N, 7.58. Found: C, 8.11; H, 2.51; N, 6.44.

% $H_2O$ (KF) = 10.86 (corresponds to a trihydrate)

Figure 2:
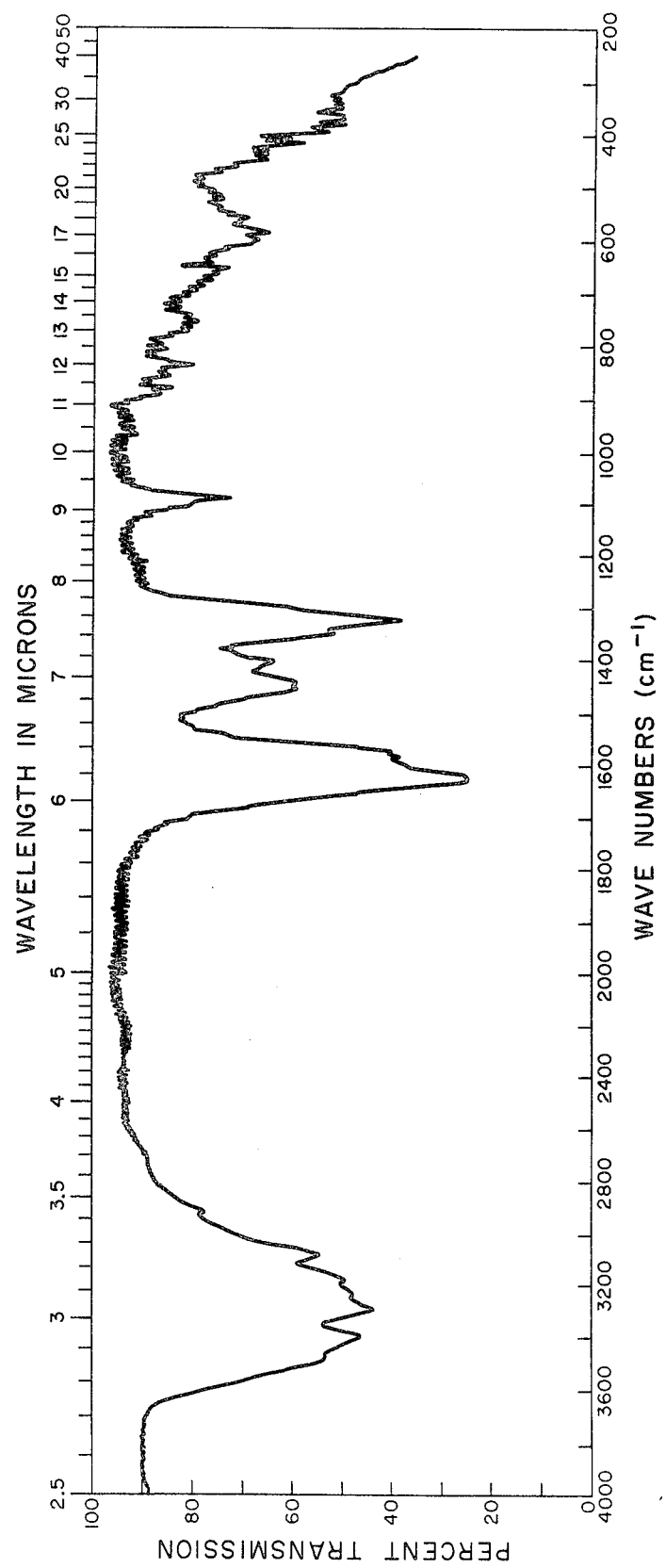
FIG. 2 shows the infrared adsorption spectrum of 2-hydroxymalonato diammine platinum (II), sodium salt

IR(KBr): see FIG. 2

UV (1.1 mg/10 ml $H_2O$): $\lambda_{max}$ = 203; A = 1.475; a = 13.3 Solubility in $H_2O$ at 22°-25° C.: >100 mg/ml.

EXAMPLE 4

2-Hydroxymalonato diammine platinum (II), sodium salt

A slurry is prepared of 1 gram of 2-hydroxymalonato diammine platinum (II) in 15-30 ml of sterile water at 40°-55° C. Over a 2 minute interval there is added with rapid stirring 2.9 ml of 1 N NaOH (1 equivalent of Na+). A pH 10-10.5 solution or near solution is obtained. The heat source is removed and the solution is stirred for an additional one minute. The solution is passed at ambient temperature through a 2 cm 0.45 micron Millipore filter to remove particles and lint. The filtrate is then lyophilized to produce the title salt. The salt may be purified by slurrying in 20 ml of acetone for 5 minutes, removing the solids by vacuum filtration (15 ml medium glass filter), washing the solids with 5 ml of acetone and vacuum drying at 50° C. for 16 hours. Yield is ~1 gram.

EXAMPLE 5

2-Hydroxymalonato diammine platinum (II), sodium salt

One gram of 2-hydroxymalonato diammine platinum (II) was slurried in 30 ml of sterile water and the mixture was warmed to 40° C. To the above reaction mixture there was added 0.88 ml of 1 N NaOH with rapid stirring over a 1-2 minute interval. A solution was obtained in an additional 0.5 minute. The solution was passed through a 0.45 micron Millipore filter. The filtrate was lyophilized for 24 hours to give the title salt as a sesquihydrate.

Properties: UV(0.1293 mg/1 in $H_2O$): $\lambda_{max}$ = 205; A = 1.42; a = 11.0

Analysis Calc'd for $C_3H_7N_2O_5Pt.Na.1.5H_2O$: C, 9.0; H, 2.7; N, 7.06. Found: C, 8.65; H, 2.22; N, 7.11.

% $H_2O$(KF) = 6.44.

IR(KBr): substantially the same as FIG. 2

EXAMPLE 6

2-Hydroxymalonato(1,2-diaminocyclohexane)platinum (II), sodium salt

A slurry is prepared of 2-hydroxymalonato(1,2-diaminocyclohexane)platinum (II) (300 mg) in 10 ml of sterile water at 20°-25° C. To the slurry there is added 0.9 ml of 1 N NaOH (36 mg of NaOH; 1 molar equivalent) and the mixture is stirred for 10 minutes. The temperature is slowly raised to 35°-45° C. whereupon a pH 10.9 solution or near solution is obtained in approximately 5 minutes of stirring. The solution (at ambient temperature) is then passed through a 0.45 micron Millipore filter to remove insoluble material. The filtrate is lyophilized to obtain the desired sodium salt. The lyophilized solid may be purified by slurrying it in 20 ml of acetone for 10 minutes, removing the solids by vacuum-filtration, washing the filter cake with 5 ml of acetone and vacuum-drying the solids for 16-24 hours at 45°-50° C. There is obtained the title sodium salt as a monohydrate in a yield of 290 mg.

Figure 3:
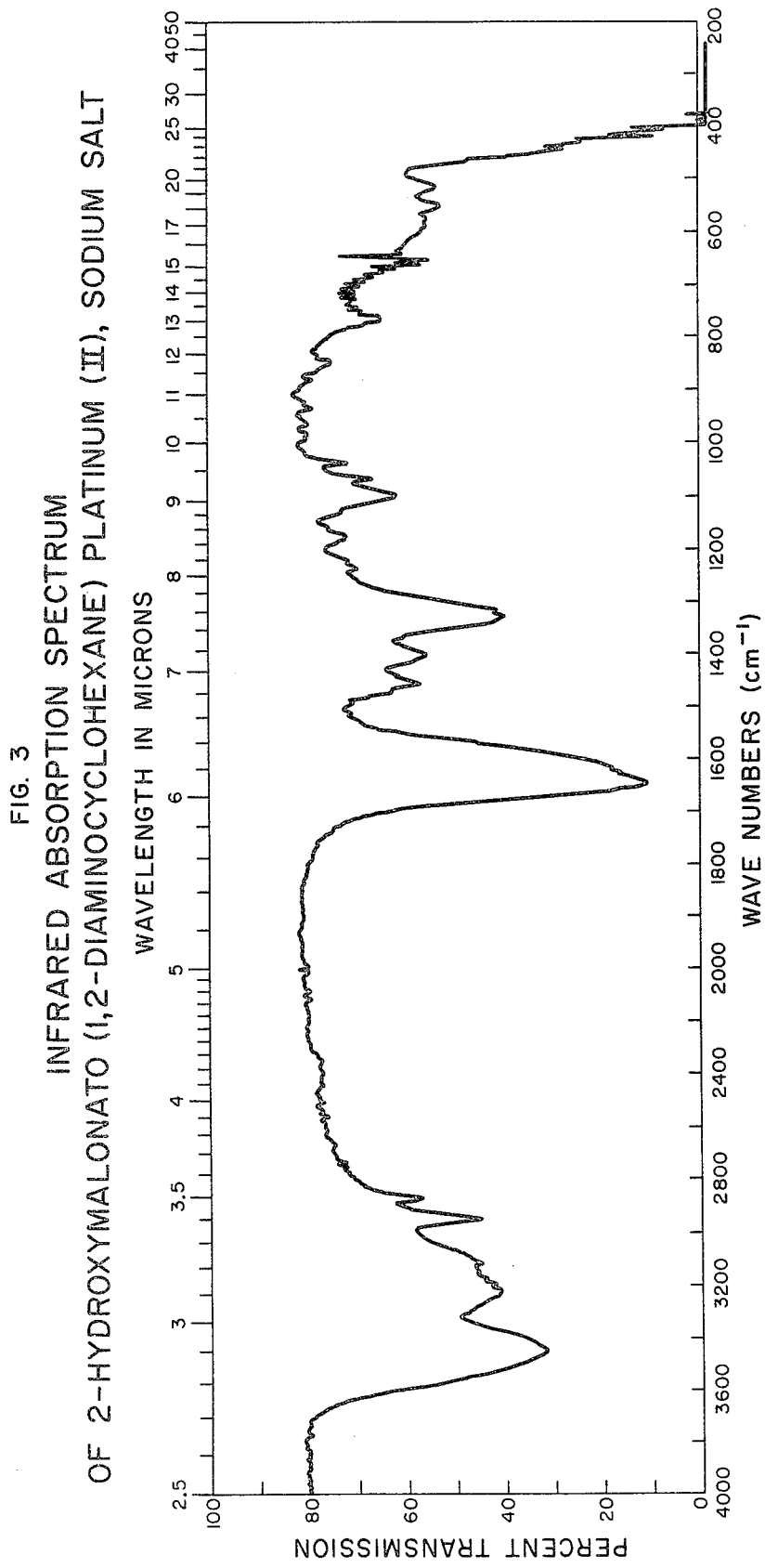
FIG. 3 shows the infrared adsorption spectrum of 2-hydroxymalonato (1,2-diaminocyclohexane)-platinum (II), sodium salt

Properties: IR as shown in FIG. 3.

| Analysis: | Found | Found (Dry basis) | Theoretical |
|---|---|---|---|
| % C | 22.04 | 22.95 | 24.03 |
| % H | 3.48 | — | 3.3 |
| % N | 5.81 | 6.03 | 6.23 |

% $H_2O$ (KF) 3.79 (theoretical for monohydrate is 3.97%). Solubility in $H_2O$ at 22°-25° C.: >13.4 mg/ml.

EXAMPLE 7

2-Hydroxymalonato(1,2-diaminocyclohexane)platinum (II), sodium salt

A slurry was prepared of 2-hydroxymalonato(1,2-diaminocyclohexane)platinum (II) (200 mg) in 5 ml of sterile water. To the slurry there was added 0.6 ml 1 N NaOH (24 mg NaOH) with stirring. A near solution was obtained in 0.5 hour. Warming to 35° C. gave a clear solution. The pH 11.59 solution was filtered through a 0.22 micron Millipore filter. The filtrate was lyophilized to apparent dryness in 6 hours. The spongy cake was stirred with 20 ml of acetone for 15 minutes. Solids were removed by vacuum-filtration, washed with 10 ml acetone and vacuum-dried at 35° C. for 16 hours to give 200 mg of the monosodium title salt.

EXAMPLE 8

2-Hydroxymalonato(1,2-diaminocyclohexane)platinum (II), ammonium salt

If in the procedure of Example 1 there is substituted an equimolar amount of 2-hydroxymalonato(1,2-diaminocyclohexane)platinum (II) for the 2-hydroxymalonato cis-diammine platinum (II) used therein, there is produced the title salt.

EXAMPLE 9

2-Hydroxymalonato (1,1-diaminomethylcyclohexane)platinum (II), sodium salt

To a slurry of 300 mg. of 2-hydroxymalonato (1,1-diaminomethylcyclohexane)platinum (II) in 15 ml. of sterile water for injection, there is added 0.67 ml of 1 N NaOH (1 molar equivalent). A near solution is obtained in about 40 minutes. The solution is passed through a 0.45 micron Millipore filter to effect clarification. The filter is washed with sterile water for injection (5 ml.) and the wash is added to the filtrate. The filtrate is then lyophilized for 24 hours (external heat at 75° F.). The lyophilized cake is slurried with 25 ml. of acetone for 10 minutes. Solids are then removed from the slurry by vacuum filtration. The solids are washed with 20 ml. of acetone and vacuum dried at 50° C. for 8-16 hours to give an expected yield of 0.29 grams of title salt.

Figure 4:
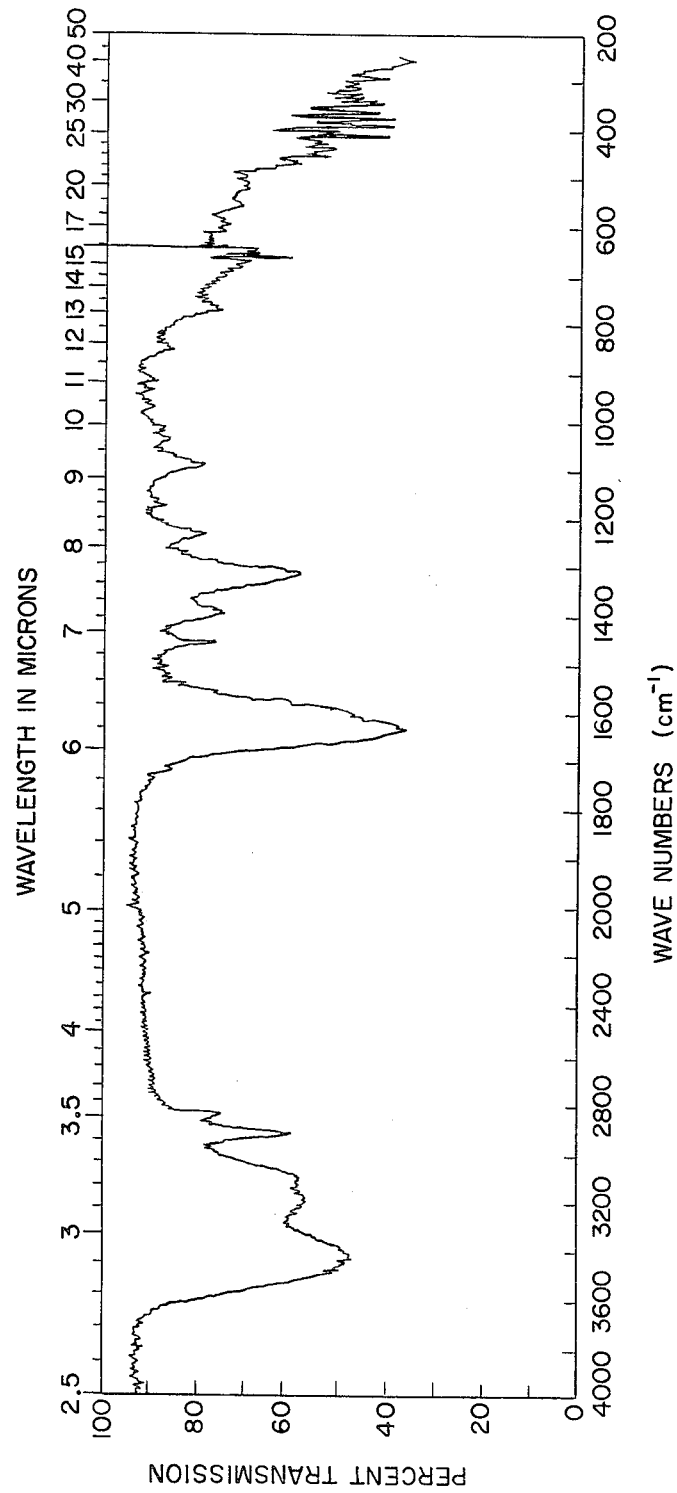
FIG. 4 shows the infrared adsorption spectrum of 2-hydroxymalonato (1,1-diaminomethylcyclohexane) platinum (II), sodium salt.

Properties: Water-solubility at room temperature = ≧100 mg/ml. (parent compound solubility ≦1.6 mg/ml) IR (KBr): as in FIG. 4

Elemental analysis: carbon—24.69%, hydrogen—4.4%, nitrogen—6.11%, % $H_2O$ (KF) = 7.85.

NMR spectrum: consistent for title product

Based on the above properties, the salt prepared according to Example 1 is monosodium 2-hydroxymalonato (1,1-diaminomethylcyclohexane)platinum (II) dihydrate.

The 2-hydroxymalonato (1,1-diaminomethylcyclohexane)platinum (II) may be prepared by the general procedures disclosed in U.K. Patent Application 2,024,823A.

EXAMPLE 10

2-Hydroxymalonato (1,1-diaminomethylcyclohexane)platinum (II), ammonium salt

If in the procedure of Example 1 there is substituted an equimolar amount of 2-hydroxymalonato (1,1-diaminomethylcyclohexane)platinum (II) for the 2-hydroxymalonato cis-diammine platinum (II) used therein, there is produced the title monoammonium salt.

We claim:

1. The ammonium salt of 2-hydroxymalonato diammine platinum (II).

2. The sodium salt of 2-hydroxymalonato diammine platinum (II).

3. The ammonium salt of 2-hydroxymalonato(1,2-diaminocyclohexane)platinum (II).

4. The sodium salt of 2-hydroxymalonato(1,2-diaminocyclohexane)platinum (II).

5. The ammonium salt of 2-hydroxymalonato (1,1-diaminomethylcyclohexane)platinum (II).

6. The sodium salt of 2-hydroxymalonato (1,1-diaminomethylcyclohexane)platinum (II).

7. A process for preparing the ammonium salt of 2-hydroxymalonato diammine platinum (II) which comprises the steps of
   (1) providing a suspension of 2-hydroxymalonato diammine platinum (II) in water;
   (2) adding to said suspension with stirring at least about one equivalent of ammonium hydroxide to form a solution; and
   (3) recovering the desired ammonium salt from said solution.

8. The process according to claim 7 wherein the salt is recovered by lyophilization.

9. The process according to claim 7 wherein the salt is recovered by solvent precipitation with acetone or isopropanol.

10. The process according to claim 7, 8 or 9 wherein the solution prepared in step (2) is filtered prior to the recovery step.

11. A process for preparing the sodium salt of 2-hydroxymalonato diammine platinum (II) which comprises the steps of
   (1) providing a suspension of 2-hydroxymalonato diammine platinum (II) in water;
   (2) adding to said suspension with stirring about one equivalent of sodium hydroxide to form a solution; and
   (3) recovering the desired sodium salt from said solution.

12. The process according to claim 11 wherein the salt is recovered by lyophilization.

13. The process according to claim 11 wherein the salt is recovered by solvent precipitation with acetone or isopropanol.

14. The process according to claim 11, 12 or 13 wherein the solution prepared in step (2) is filtered prior to the recovery step.

15. A process for preparing the ammonium salt of 2-hydroxymalonato(1,2-diaminocyclohexane)platinum (II) which comprises the steps of
   (1) providing a suspension of 2-hydroxymalonato(1,2-diaminocyclohexane)platinum (II) in water;
   (2) adding to said suspension with stirring at least about one equivalent of ammonium hydroxide to form a solution; and
   (3) recovering the desired ammonium salt from said solution.

16. The process according to claim 15 wherein the salt is recovered by lyophilization.

17. The process according to claim 15 wherein the salt is recovered by solvent precipitation with acetone or isopropanol.

18. The process according to claim 15, 16 or 17 wherein the solution prepared in step (2) is filtered prior to the recovery step.

19. A process for preparing the sodium salt of 2-hydroxymalonato(1,2-diaminocyclohexane)platinum (II) which comprises the steps of
   (1) providing a suspension of 2-hydroxymalonato(1,2-diaminocyclohexane)platinum (II) in water;
   (2) adding to said suspension with stirring about one equivalent of sodium hydroxide to form a solution; and
   (3) recovering the desired sodium salt from said solution.

20. The process according to claim 19 wherein the salt is recovered by lyophilization.

21. The process according to claim 19 wherein the salt is recovered by solvent precipitation with acetone or isopropanol.

22. The process according to claim 19, 20 or 21 wherein the solution prepared in step (2) is filtered prior to the recovery step.

23. A process for preparing the ammonium salt of 2-hydroxymalonato (1,1-diaminomethylcyclohexane)-platinum (II) which comprises the steps of
   (1) providing a suspension of 2-hydroxymalonato(1,1-diaminomethylcyclohexane)platinum (II) in water;
   (2) adding to said suspension with stirring at least about one equivalent of ammonium hydroxide to form a solution; and
   (3) recovering the desired ammonium salt from said solution.

24. The process according to claim 23 wherein the salt is removed by lyophilization.

25. The process according to claim 23 wherein the salt is recovered by solvent precipitation with acetone or isopropanol.

26. The process according to claim 23, 24 or 25 wherein the solution in step (2) is filtered prior to the recovery step.

27. A process for preparing the sodium salt of 2-hydroxymalonato (1,1-diaminomethylcyclohexane)-platinum (II) which comprises the steps of
   (1) providing a suspension of 2-hydroxymalonato (1,1-diaminomethylcyclohexane)platinum (II) in water;
   (2) adding to said suspension with stirring about one equivalent of sodium hydroxide to form a solution; and
   (3) recovering the desired sodium salt from said solution.

28. The process according to claim 27 wherein the salt is recovered by lyophilization.

29. The process according to claim 27 wherein the salt is recovered by solvent precipitation with acetone or isopropanol.

30. The process according to claim 27, 28 or 29 wherein the solution prepared in step (2) is filtered prior to the recovery step.

* * * * *